US009212105B2

United States Patent
Qi et al.

(10) Patent No.: US 9,212,105 B2
(45) Date of Patent: Dec. 15, 2015

(54) PROCESSES FOR PRODUCING AT LEAST ONE LIGHT OLEFIN

(75) Inventors: Guozhen Qi, Shanghai (CN); Siqing Zhong, Shanghai (CN); Hongtao Wang, Shanghai (CN); Yongming Jin, Shanghai (CN)

(73) Assignees: Shanghai Research Institute of Petrochemical Technology, Sinopec, Shanghai (CN); China Petroleum & Chemical Corporation, Beijing (CN)

( * ) Notice: Subject to any disclaimer, the term of this patent is extended or adjusted under 35 U.S.C. 154(b) by 186 days.

(21) Appl. No.: 13/039,388

(22) Filed: Mar. 3, 2011

(65) Prior Publication Data

US 2011/0218373 A1  Sep. 8, 2011

(30) Foreign Application Priority Data

Mar. 3, 2010 (CN) .......................... 2010 1 0116474

(51) Int. Cl.
| | | |
|---|---|---|
| C07C 1/20 | (2006.01) | |
| C07C 1/22 | (2006.01) | |
| C07C 4/08 | (2006.01) | |
| C07C 11/04 | (2006.01) | |
| C07C 11/06 | (2006.01) | |

(52) U.S. Cl.
CPC ... *C07C 1/20* (2013.01); *C07C 4/08* (2013.01); *C07C 11/04* (2013.01); *C07C 11/06* (2013.01)

(58) Field of Classification Search
None
See application file for complete search history.

(56) References Cited

U.S. PATENT DOCUMENTS

| | | | | |
|---|---|---|---|---|
| 4,171,286 | A | * | 10/1979 | Dight et al. ...................... 502/66 |
| 4,370,222 | A | * | 1/1983 | McGovern et al. ........... 208/113 |
| 4,444,651 | A | * | 4/1984 | Myers et al. ............. 208/120.01 |
| 4,499,327 | A | | 2/1985 | Kaiser |

(Continued)

FOREIGN PATENT DOCUMENTS

| | | |
|---|---|---|
| CN | 1438296 | 8/2003 |
| CN | 1723262 | 1/2006 |

(Continued)

OTHER PUBLICATIONS

Bishop, Petroleum hydrocarbons and petroleum hydrocarbons measurements, May 1997, Massachusetts Department of Environmental Protection, Board of Registration of Hazardous Waste Site Cleanup Professionals.*

(Continued)

*Primary Examiner* — In Suk Bullock
*Assistant Examiner* — Youngsul Jeong
(74) *Attorney, Agent, or Firm* — Finnegan, Henderson, Farabow, Garrett & Dunner, L.L.P.

(57) ABSTRACT

A process for producing at least one light olefin comprising: (a) contacting a first raw material comprising methanol with a least one catalyst in a first reaction zone to produce at least one light olefin and at least one inactivated catalyst; (b) transporting the at least one inactivated catalyst to a first regeneration zone to produce at least one first regenerated catalyst, and transporting a portion of the at least one first regenerated catalyst to the first reaction zone; (c) transporting another portion of the at least one first regenerated catalyst to a second regeneration zone to obtain at least one second regenerated catalyst; and (d) transporting the at least one second regenerated catalyst to a second reaction zone, and contacting the at least one second regenerated catalyst with a second raw material comprising C4 olefins to produce a product stream II comprising at least one light olefin.

13 Claims, 1 Drawing Sheet

(56) References Cited

U.S. PATENT DOCUMENTS

| | | | |
|---|---|---|---|
| 5,447,622 A * | 9/1995 | Kerby et al. | 208/78 |
| 5,914,433 A * | 6/1999 | Marker | 585/313 |
| 6,166,282 A | 12/2000 | Miller | |
| 2006/0025646 A1* | 2/2006 | Fung et al. | 585/639 |
| 2007/0293709 A1* | 12/2007 | Iaccino et al. | 585/312 |
| 2010/0179365 A1* | 7/2010 | Ito et al. | 585/639 |
| 2010/0331596 A1* | 12/2010 | Xie et al. | 585/639 |

FOREIGN PATENT DOCUMENTS

| | | |
|---|---|---|
| CN | 101239869 | 8/2008 |
| CN | 101265150 | 9/2008 |
| CN | 101270023 | 9/2008 |
| CN | 101333141 | 12/2008 |
| CN | 101402538 | 4/2009 |
| CN | 101402539 | 4/2009 |
| WO | WO 2004/037950 | 5/2004 |
| WO | WO 2009024012 A1 * | 2/2009 |

OTHER PUBLICATIONS

Li-Ping Ye et al., "Synthesis of SAPO-34 Molecular Sieves and Their Catalytic Performances in Methanol-to-Olefins Reaction," Journal of East China University of Science and Technology (Natural Science Edition) vol. 36, No. 1, pp. 6-12.

* cited by examiner

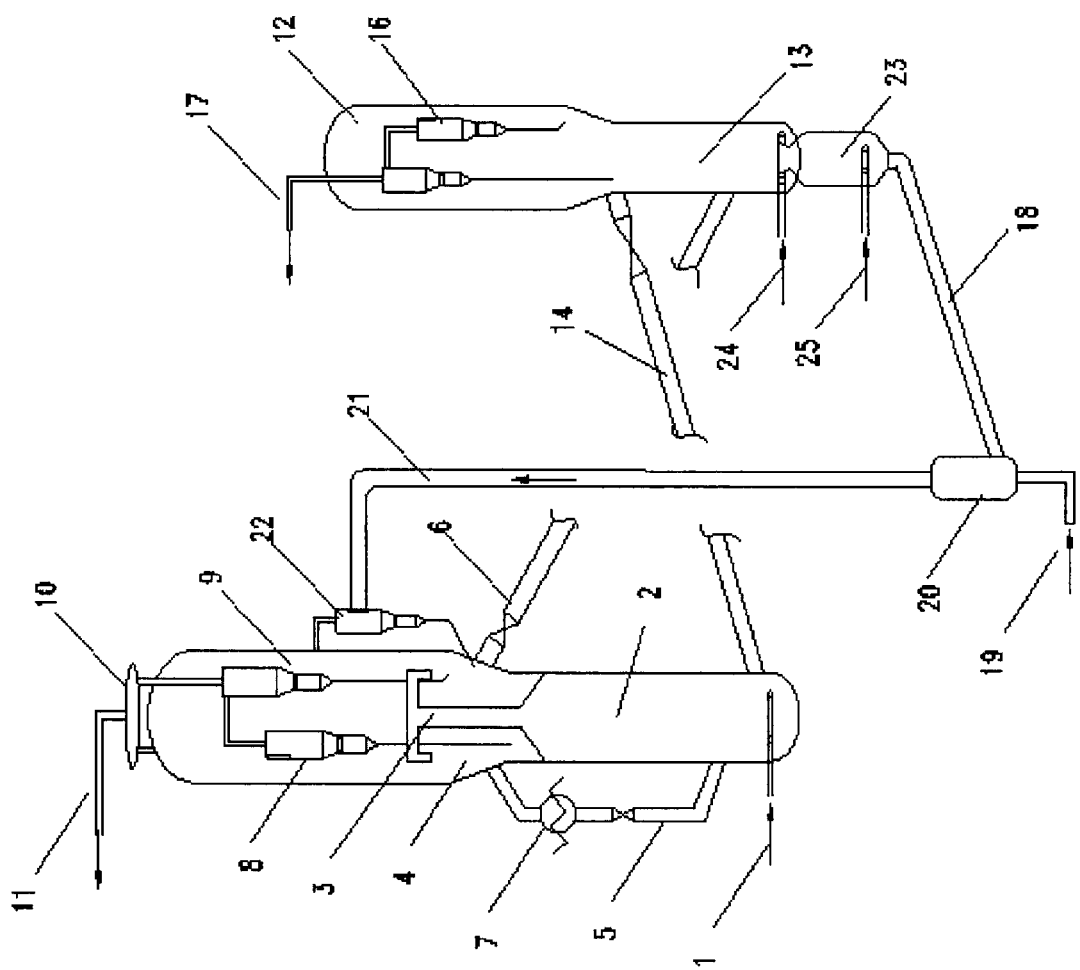

PROCESSES FOR PRODUCING AT LEAST ONE LIGHT OLEFIN

Disclosed herein are processes for producing at least one light olefin.

Light olefins, i.e. ethylene and propylene, are two important basic chemical materials with an increasing demand. Generally, ethylene and propylene are produced from petroleum. Due to limited supply and higher price of petroleum resource, the cost of producing ethylene and propylene from petroleum resource is continuously increasing. Recently, techniques for preparing ethylene and propylene by conversion of petroleum alternatives have been developed. Oxygen-containing compounds such as alcohols (methanol, ethanol), ethers (dimethyl ether, methyl ethyl ether), esters (dimethyl carbonate, methyl formate) and the like, which can be converted from petroleum alternatives such as coal, natural gas, biomass and the like. Some oxygen-containing compounds, such as methanol, can be produced from coal or natural gas on a large scale, reaching to production scales of millions of tons. Due to the abundant supply of such oxygen-containing compounds, in combination with the more economically efficient technique of olefin production by conversion from petroleum alternatives, the Oxygenate To Olefins processes (OTO), such as the Methanol to Olefins processes (MTO), have drawn more and more attention. Examples of such processes are disclosed in U.S. Pat. Nos. 4,499,327 and 6,166,282, and CN1723262.

To ensure a higher selectivity of light olefin in a catalytic process, a certain amount of carbon deposit is required on the catalyst. Moreover, the process of converting methanol or dimethyl ether into light olefins is sensitive to parameters such as reaction temperature and the like. Hence, in the production of light olefins, heterogeneous distribution of the carbon deposit on the catalyst and great fluctuations of the reaction temperature in the reaction zone can cause problems.

One aspect of the present disclosure is to address low selectivity of light olefins and also to provide a process for producing at least one light olefin. High selectivity of light olefins and economic efficiency for manufacturing light olefins are desired.

Another aspect of the present disclosure is to provide a process for producing at least one light olefin, comprising:
(a) contacting a first raw material comprising methanol with at least one catalyst comprising at least one silicon-aluminophosphate molecular sieve in a first reaction zone to produce a product stream I comprising at least one light olefin and at least one inactivated catalyst;
(b) transporting the at least one inactivated catalyst to a first regeneration zone to produce at least one first regenerated catalyst, and transporting a portion of the at least one first regenerated catalyst to the first reaction zone, wherein the at least one first regenerated catalyst comprises a carbon deposit present in an amount ranging from about 0.8% to about 2.5% by weight relative to the total weight of the at least one first regenerated catalyst;
(c) transporting another portion of the at least one first regenerated catalyst to a second regeneration zone to obtain at least one second regenerated catalyst, wherein the at least one second regenerated catalyst comprises a carbon deposit present in an amount of less than about 0.2% by weight relative to the total weight of the second regenerated catalyst;
(d) transporting the at least one second regenerated catalyst to a second reaction zone, and contacting the at least one second regenerated catalyst with a second raw material comprising at least one C4 olefin to produce a product stream II comprising at least one light olefin.

In some embodiments, the process disclosed herein for producing at least one light olefin further comprises transporting the product stream II to a gas-solid separation zone; and combining the product stream II from the gas-solid separation zone with the product stream I.

In some embodiments, the at least one silicon-aluminophosphate molecular sieve is illustratively chosen from SAPO-5, SAPO-11, SAPO-17, SAPO-18, SAPO-34, SAPO-35, SAPO-44 and SAPO-56, such as SAPO-34.

In some embodiments, the first reaction zone is a fast fluidized bed, and the second reaction zone is a riser.

In some embodiments, the second raw material that comprises at least one C4 olefin further comprises methanol and/or dimethyl ether.

In some embodiments, at least one oxygen depleted regeneration is conducted in the first regeneration zone, and at least one oxygen enriched regeneration is conducted in the second regeneration zone.

In some embodiments, at least one CO combustion adjuvant is added into the first regeneration zone.

In some embodiments, the reaction in the first reaction zone is conducted under the conditions of (1) a gauge pressure ranging from about 0.01 MPa to about 0.3 MPa, (2) a temperature ranging from about 400° C. to about 500° C., (3) a weight hourly space velocity of the raw material ranging from about 6 $h^{-1}$ to about 25 $h^{-1}$, and (4) an average amount of the carbon deposit of the catalyst in the first reaction zone ranging from about 1% to about 4% by weight relative to the total amount of the catalyst.

In some embodiments, the reaction in the second reaction zone is conducted under the conditions of (1) a gauge pressure ranging from about 0.01 MPa to about 0.3 MPa, (2) a temperature ranging from about 500° C. to about 650° C., and a (3) gaseous phase linear speed ranging from about 5 m/s to about 12 m/s.

The weight hourly space velocity used herein is defined as the amount of the feedstock fed within a certain time divided by the amount of active ingredients (such as molecular sieves) in the catalyst in the reaction zone.

The average amount of the carbon deposit used herein is calculated by dividing the weight of the carbon deposit on the catalyst by the weight of the catalyst. The weight of the carbon deposit on the catalyst is measured according to the method as follows: mixing the catalysts having carbon deposit homogeneously, weighing from about 0.1 gram to about 1 gram of the catalysts having carbon deposit, combusting the catalysts having carbon deposit in a high-temperature carbon analyzer, determining the weight of carbon dioxide produced by combustion with infrared measurement, so as to obtain the weight of the carbon deposit on the catalysts.

In some embodiments, the at least one silicon-aluminophosphate molecular sieve used herein can, for example, be prepared by:
(i) preparation of a molecular sieve precursor: mixing, in a molar ratio, about 0.03-0.6 R:(about 0.01-0.98 Si:about 0.01-0.6 Al:about 0.01-0.6 P):about 2-500 $H_2O$, together to form a molecular sieve precursor;
(ii) crystallizing the molecular sieve precursor at a certain temperature, for example, from about 100° C. to about 250° C., for a certain period of time, such as from about 1 hour to about 10 hours, wherein R is chosen from templating agents, to obtain the SAPO molecular sieves; and
(iii) the resulting SAPO molecular sieves are mixed with at least one binder, spray-dried, and calcined to obtain the SAPO catalyst, wherein the binder is generally in an amount ranging from about 10% to about 90% by weight of the catalyst.

In some embodiments, the at least one CO combustion adjuvant used herein is chosen from fluidized bed catalysts supported by at least one noble metal capable of catalyzing the oxidation of CO to $CO_2$, wherein the at least one noble metal is chosen, for example, from Pt and Pd, and the weight ratio of the CO combustion adjuvant to the total weight of the catalyst in the first regeneration zone is not greater than about 1:100.

In some embodiments, during the reaction of converting the oxygen-containing compounds into at least one light olefin, a certain amount of carbon, for example, from about 1% to about 4% by weight, needs to be carried on the catalyst, so as to increase the selectivity of the light olefins. In some embodiments, the catalyst to be regenerated is mixed with the at least first and/or the at least second regenerated catalyst so as to obtain a desired amount of carbon deposit. The inventors have found that a certain amount of carbon deposit on the regenerated catalyst may decrease the carbon difference from the catalyst to be regenerated, and mixing can effectively increase the selectivity of the light olefins.

In some embodiments, at least one oxygen depleted regeneration is conducted in the first regeneration zone, in which the oxygen concentration is strictly controlled to ensure the incomplete combustion of carbon deposit on the at least one first regenerated catalyst. Then, the at least one first regenerated catalyst having a certain amount of carbon deposit is directly recycled to the first reaction zone, and further mixed with the catalyst to be regenerated to obtain a desired average amount of the carbon deposit in the first reaction zone. For example, the at least one first regenerated catalyst and the catalyst to be regenerated in the first reaction zone may be mixed at a weight ratio ranging from about 0.2:1 to about 2:1.

In certain embodiments, some by-products, such as hydrocarbons comprising more than 4 carbon atoms will be unavoidably produced during the preparation of olefins from methanol. Those hydrocarbons comprising more than 4 carbon atoms generally have a higher olefin content and can be catalytically cracked into ethylene and propylene. However, catalysts that can be used for cracking hydrocarbons comprising more than 4 carbon atoms generally have a high catalytic activity.

In some embodiments, an oxygen depleted regeneration is conducted at the first regeneration zone, and the at least one regenerated catalyst produced therein is introduced into the second regeneration zone for the oxygen enriched regeneration, so as to completely combust the carbon deposit carried by the catalyst and to recover the initial activity of the catalyst. Then, such completely regenerated catalyst is introduced into the second reaction zone and contacted with the feedstock comprising at least one C4 olefin to further crack hydrocarbons comprising more than 4 carbon atoms into ethylene and propylene. Meanwhile, carbon deposit is formed on the catalyst in the second reaction zone. In one exemplary embodiment, to increase the selectivity of the light olefins in the first reaction zone, the catalyst on which the carbon deposit is formed is fed into the first reaction zone via the riser and the circulating pipe of the catalyst to be regenerated.

In some embodiments, a regenerator comprising the first regeneration zone and the second regeneration zone may provide two kinds of carbon deposits having different activities, which effectively ensure the processes of preparing at least one olefin from methanol and cracking hydrocarbons comprising more than 4 carbon atoms, thereby maximizing the yield of light olefins in the product.

As used herein, the oxygen depleted regeneration generally means having a low oxygen concentration in the regeneration zone that is insufficient to combust all the carbon deposit, so that it is an incomplete regeneration reaction. On the contrary, the oxygen enriched regeneration means having an excessive amount of oxygen concentration that is sufficient to combust all the carbon deposit, so that it is a complete regeneration reaction.

In one embodiment, the at least one silicon-aluminophosphate molecular sieve is chosen from SAPO-5, SAPO-11, SAPO-17, SAPO-18, SAPO-34, SAPO-35, SAPO-44 and SAPO-56; the first reaction zone comprises a fast fluidized bed, and the second reaction zone comprises a riser; the second raw material comprises at least one C4 olefin further comprising methanol and/or dimethyl ether; the oxygen depleted regeneration is conducted in the first regeneration zone, and the oxygen enriched regeneration is conducted in the second regeneration zone; and a CO combustion adjuvant is added into the first regeneration zone.

In another exemplary embodiment, the first regeneration zone and second regeneration zone are positioned in one regenerator. The reaction in the first reaction zone is conducted under conditions comprising: (1) a gauge pressure ranging from about 0.01 MPa to about 0.3 MPa, (2) a temperature ranging from about 400° C. to about 500° C., (3) a weight hourly space velocity of the raw materials ranging from about 6 $h^{-1}$ to about 25 $h^{-1}$, and (4) an average amount of carbon deposit of the catalyst in the first reaction zone ranging from about 1% to about 4% by weight relative to the total weight of the catalyst; and the second reaction zone is conducted under conditions comprising: (1) a gauge pressure ranging from about 0.01 MPa to about 0.3 MPa, (2) a temperature ranging from about 500° C. to about 650° C., and (3) a gaseous phase linear speed ranging from about 5 m/s to about 12 m/s.

BRIEF DESCRIPTION OF THE DRAWING

FIG. 1 is the representative schematic view of one non-limiting embodiment of the process according to the present disclosure.

In FIG. 1, 1 represents the feedstock in the first reaction zone of a reactor;

2 represents the first reaction zone of the reactor;

3 represents the gas-solid fast separation device;

4 represents the stripping zone;

5 represents the circulating sloped pipe for the catalyst to be regenerated;

6 represents the pipe for conveying the catalyst to be regenerated to the regenerator;

7 represents the heat exchanger;

8 represents the gas-solid cyclone separator of the reactor;

9 represents the gas-solid separation zone of the reactor;

10 represents the gas collecting chamber;

11 represents the gas outlet pipe;

12 represents the regenerator;

13 represents the first regeneration zone;

14 represents the pipe for conveying the regenerated catalyst from the first regeneration zone to the first reaction zone 2;

16 represents the gas-solid cyclone separator of the regenerator;

17 represents the outlet pipe for the flue gas from the regenerator;

18 represents the pipe for conveying the regenerated catalyst from the second regeneration zone to the second reaction zone;

19 represents the feedstock inlet pipe of the second reaction zone;

20 represents the mixing section at the lower part of the second reaction zone;

21 represents the second reaction zone;

22 represents the gas-solid cyclone separator at the outlet of the second reaction zone;

23 represents the second regeneration zone;

24 represents the inlet pipe for the regenerating medium at the bottom of the first regeneration zone; and 25 represents the inlet pipe for the regenerating medium at the bottom of the second regeneration zone.

In some embodiments, the process for producing at least one light olefin can be shown in FIG. 1 and comprises the following steps: A feedstock comprising methanol is fed into the first reaction zone 2 of the reactor via the feedstock pipe 1. The feedstock is then contacted and reacted with catalysts comprising at least one molecular sieve to produce a product comprising at least one light olefin. The product comprising light olefins and the catalysts to be regenerated are fed into the separation zone 9 of the reactor via the gas-solid fast separation device 3, wherein most of the catalysts separated from the gas-solid fast separation device 3 are fed into the stripping zone 4; the gaseous product and a part of the catalysts not separated in the gas-solid fast separation device 3 are fed into the cyclone separator 8 for further separation. In the cyclone separator 8, the catalysts are recycled to the stripping zone 4 via the dipleg of the cyclone separator 8, and the gaseous product is fed into the gas collecting chamber 10 and then into the subsequent separation section via the outlet pipe 11. The catalysts to be regenerated, which are separated by the gas-solid fast separation device 3 and the cyclone separator 8, are divided into two parts after stripping, wherein one part of the catalysts passes through the heat exchanger 7 and then to the bottom of the first reaction zone 2 via the circulating sloped pipe 5; and the other part of the catalysts is fed into the first regeneration zone 13 of the regenerator 12 via the catalyst-conveying pipe 6 for coke burning regeneration. The flue gas produced by coke burning flows through the cyclone separator 16 and into the subsequent energy recovery system via the outlet pipe 17 for the flue gas, and the catalysts regenerated in the first regeneration zone 13 are recycled to the first reaction zone 2 via the pipe 14 for conveying catalysts. The remaining catalysts in the first regeneration zone 13 are fed into the second regeneration zone 23, and the regenerated catalysts are fed into the mixing section 20 at the lower part of the second reaction zone 21 via the pipe 18 and mixed with the feedstock coming from the feedstock inlet pipe 19. The catalysts and product are fed into the separation zone 9 of the reactor.

The embodiments of the present disclosure described herein are representative and not limitative.

EXAMPLES 1-2

In the fast fluidized bed reaction device shown in FIG. 1, the first reaction zone is a fast fluidized bed, the second reaction zone is a riser, and the first and second regeneration zones are both turbulent fluidized beds. A feedstock comprising methanol was fed into the first reaction zone of the reactor and reacted with catalysts (shown in Table 1) to produce at least one light olefin, and the gaseous product was fed into the subsequent separation section. About 65% by weight of the separated, catalyst to be regenerated was recycled to the first reaction zone after stripping, and the remaining about 35% by weight was fed into the first regeneration zone for coke burning regeneration. About 32% by weight of the catalyst regenerated in the first regeneration zone was recycled to the first reaction zone, and about 68% by weight was fed into the second regeneration zone. The catalyst regenerated in the second regeneration zone was fed into the second reaction zone and mixed with the feedstock, and the catalyst and product produced in the second reaction zone were fed into the separation zone of the reactor.

The first reaction zone has an average temperature of 500° C., and a gauge reaction pressure of 0.01 MPa. Pure methanol was fed at a feed rate of 4.2 ton/h, wherein the methanol has a weight hourly space velocity of 25 $h^{-1}$, and the catalyst has an average carbon deposit amount of about 4% by weight relative to the total weight of the catalyst. The catalyst type can be found in Table 1. The stripping medium in the stripping zone was water vapor.

The second reaction zone has a reaction temperature of 650° C., and the feedstock was the mixed C4 olefins containing olefins in an amount of about 87% by weight and fed at a feed rate of 0.4 ton/h, wherein the gauge pressure was 0.02 MPa, and the gaseous phase linear speed was 12 m/s.

A palladium/alumina CO combustion adjuvant was added into the first regeneration zone, wherein palladium was in an amount of about 0.05% by weight, in an amount of about 1% by weight relative to the reserve amount of the catalyst in the first regeneration zone.

The carbon deposit of the regenerated catalyst in the first regeneration zone was in an amount of about 2.5% by weight relative to the total weight of the catalyst, and the carbon deposit of the regenerated catalyst in the second regeneration zone was in an amount of about 0.05% by weight relative to the total weight of the catalyst.

While maintaining the flow control stability of the catalyst, samples were taken respectively at the outlet of the second reaction zone and at the outlet of the separation zone of the reactor for qualitative and quantitative analyses, so as to determine the product composition in the reaction zone. The product was analyzed with gas chromatography, and the test results obtained are reported in Table 1.

TABLE 1

| Parameters | Catalyst Type | Yield of light olefin at the outlet of the first reaction zone (carbon basis), % by weight | Yield of light olefin at the outlet of the second reaction zone (carbon basis), % by weight | Total yield of light olefin, % by weight (aqueous) |
|---|---|---|---|---|
| Example 1 | SAPO-18 | 79.12 | 35.87 | 35.72 |
| Example 2 | SAPO-34 | 81.58 | 38.91 | 36.97 |

EXAMPLE 3

Except as stated otherwise below, the conditions as described in Example 2 were followed.

About 42% by weight of the catalyst to be regenerated was recycled to the first reaction zone after stripping, and about 58% by weight thereof was fed into the first regeneration for coke burning regeneration. About 17% by weight of the catalyst regenerated in the first regeneration zone was recycled to the first reaction zone, and about 83% by weight was fed into the second regeneration zone.

The first reaction zone has an average temperature of 400° C., and a gauge reaction pressure of 0.3 MPa. Pure methanol was fed at a feed rate of 4.2 ton/h and has a weight hourly space velocity of 6 h$^{-1}$. The catalyst was SAPO-34 and has an average carbon deposit amount of about 1% by weight.

The second reaction zone has a reaction temperature of 500° C., and the feedstock was the mixed C4 olefins containing olefins in an amount of about 87% by weight and fed at a feed rate of 0.4 ton/h, wherein the gauge reaction pressure was 0.3 MPa, and the gaseous phase linear speed was 5 m/s.

A palladium/alumina CO combustion adjuvant containing palladium in an amount of about 0.05% by weight was added into the first regeneration zone in an amount of 1% by weight relative to the reserve amount of the catalyst in the first regeneration zone.

The regenerated catalyst in the first regeneration zone has a carbon deposit amount of about 0.8% by weight relative to the total weight of the catalyst; and the regenerated catalyst in the second regeneration zone has a carbon deposit amount of 0.03% by weight relative to the total weight of the catalyst.

Regarding results, the yield of light olefin in carbon basis at the outlet of the first reaction zone was about 78.92% by weight; the yield of light olefin in carbon basis at the outlet of the second reaction zone was about 28.61% by weight; and the total yield of light olefin was about 32.75% by weight (aqueous).

EXAMPLE 4

Except as stated otherwise below, the conditions as described in Example 2 were followed.

The first reaction zone had an average temperature of 460° C., and a gauge reaction pressure of 0.15 MPa. Pure methanol was fed at a feed rate of 4.2 ton/h and had a weight hourly space velocity of 10 h$^{-1}$. The catalyst was SAPO-34 and had an average carbon deposit amount of about 2.7% by weight.

The second reaction zone had a reaction temperature of 620° C., and the feedstock was the mixed C4 olefins containing olefins in an amount of about 87% by weight and fed at a feed rate of 0.4 ton/h, wherein the gauge reaction pressure was 0.15 MPa, and the gaseous phase linear speed was 7 m/s.

The regenerated catalyst in the first regeneration zone had a carbon deposit amount of about 1.5% by weight relative to the total weight of the catalyst; and the regenerated catalyst in the second regeneration zone had a carbon deposit amount of about 0.05% by weight relative to the total weight of the catalyst.

The yield of light olefin in carbon basis at the outlet of the first reaction zone was about 82.54% by weight; the yield of light olefin in carbon basis at the outlet of the second reaction zone was about 40.53% by weight; and the total yield of light olefin was about 37.39% by weight (aqueous).

EXAMPLE 5

Except as stated otherwise below, the conditions as described in Example 4 were followed.

The mixtures of the mixed C4 olefins and methanol with dimethyl ether were fed into the second reaction zone, wherein the olefins in the mixed C4 were in an amount of about 87% by weight; the mixed C4:methanol:dimethyl ether was present in a weight ration of 10:2:1. The total mass throughput of the feedstock in the second reaction zone was 0.4 ton/h, and the regenerated catalyst in the second regeneration zone has a carbon deposit amount of about 0.2% by weight relative to the total weight of the catalyst.

The yield of light olefin in carbon basis at the outlet of the first reaction zone was about 82.39% by weight; the yield of light olefin in carbon basis at the outlet of the second reaction zone was about 41.07% by weight; and the total yield of light olefin was about 37.73% by weight (aqueous).

The processes of the present disclosure can be applied industrially to produce at least one light olefin.

What is claimed is:

1. A process for producing at east one light olefin, comprising:
    (a) contacting a first raw material comprising methanol with at least one catalyst comprising at least one silicon-aluminophosphate molecular sieve in a first reaction zone to produce a product stream I comprising at least one light olefin and at least one inactivated catalyst;
    (b) transporting a portion of the at least one inactivated catalyst back to the first reaction zone; and transporting another portion of the at least one inactivated catalyst to a first regeneration zone to produce at least one first regenerated catalyst, and transporting a portion of the at least one first regenerated catalyst to the first reaction zone, wherein the at least one first regenerated catalyst comprises a carbon deposit present in an amount ranging from about 1.5% to about 2.5% by weight relative to the total weight of the at least one first regenerated catalyst;
    (c) transporting another portion of the at least one first regenerated catalyst to a second regeneration zone to obtain at least one second regenerated catalyst, wherein the at least one second regenerated catalyst comprises a carbon deposit present in an amount of less than about 0.2% by weight relative to the total weight of the at least one second regenerated catalyst;
    (d) transporting the at least one second regenerated catalyst to a second reaction zone, and contacting the at least one second regenerated catalyst with a second raw material comprising C4 olefins to produce a product stream II comprising at least one light olefin and at least one carbon-deposited second regenerated catalyst; and
    (e) transporting an amount of the at least one carbon-deposited second regenerated catalyst to the first reaction zone,
    wherein the first reaction zone has an average amount of the carbon deposit ranging from about 2.7% to about 4% by weight relative to the total amount of the catalyst.

2. The process for producing at least one light olefin according to claim 1, wherein the at least one silicon-aluminophosphate molecular sieve is chosen from SAPO-5, SAPO-11, SAPO-17, SAPO-18, SAPO-34, SAPO-35, SAPO-44 and SAPO-56.

3. The process for producing at least one light olefin according to claim 1, wherein the first reaction zone comprises a fast fluidized bed.

4. The process for producing at least one light olefin according to claim 1, wherein the second reaction zone comprises a riser.

5. The process for producing at least one light olefin according to claim 2, wherein the at least one silicon-aluminophosphate molecular sieve is SAPO-34.

6. The process for producing at least one light olefin according to claim 1, wherein the second raw material further comprises methanol and/or dimethyl ether.

7. The process for producing at least one light olefin according to claim 1, wherein at least one oxygen depleted regeneration is conducted in the first regeneration zone.

8. The process for producing at least one light olefin according to claim 1, wherein at least one oxygen enriched regeneration is conducted in the second regeneration zone.

9. The process for producing at least one light olefin according to claim 1, wherein at least one CO combustion adjuvant is added into the first regeneration zone.

10. The process for producing at least one light olefin according to claim 1, wherein the first regeneration zone and the second regeneration zone are positioned in one regenerator.

11. The process for producing at least one light olefin according to claim 1, wherein the first reaction zone comprises the following reaction conditions:
- a gauge pressure ranging from about 0.01 MPa to about 0.3 MPa,
- a temperature ranging from about 400° C. to about 500° C.,
- a weight hourly space velocity of the first raw material ranging from about 6 h$^{-1}$ to about 25 h$^{-1}$, and
- an average amount of carbon deposit of the catalyst in the first reaction zone ranging from about 2.7% to about 4% by weight relative to the total weight of the catalyst.

12. The process for producing at least one light olefin according to claim 1, wherein the second reaction zone comprises the following reaction conditions:
- a gauge pressure ranging from about 0.01 MPa to about 0.3 MPa,
- a temperature ranging from about 500° C. to about 650° C., and
- a gaseous phase linear speed ranging from about 5 m/s to about 12 m/s.

13. The process for producing at least one light olefin according to claim 1, further comprising:
- transporting the product stream II to a gas-solid separation zone; and
- combining the product stream II from the gas-solid separation zone with the product stream I.

* * * * *

UNITED STATES PATENT AND TRADEMARK OFFICE
CERTIFICATE OF CORRECTION

| | |
|---|---|
| PATENT NO. | : 9,212,105 B2 |
| APPLICATION NO. | : 13/039388 |
| DATED | : December 15, 2015 |
| INVENTOR(S) | : Qi et al. |

It is certified that error appears in the above-identified patent and that said Letters Patent is hereby corrected as shown below:

Title page, item 57, lines 2-3, "with a least one catalyst" should read -- with at least one catalyst --.

Claims

Claim 1, col. 8, lines 6, "producing at east one" should read -- producing at least one --.

Signed and Sealed this
Seventeenth Day of May, 2016

Michelle K. Lee
*Director of the United States Patent and Trademark Office*